US011040080B2

(12) United States Patent
Ueda et al.

(10) Patent No.: US 11,040,080 B2
(45) Date of Patent: Jun. 22, 2021

(54) FEED FOR DOMESTIC ANIMALS OR SUPPLEMENT FOR DOMESTIC ANIMALS, GROWTH-PROMOTING AGENT FOR BACTERIUM OF GENUS *LACTOBACILLUS*, AND METHOD FOR PROMOTING GROWTH OF BACTERIUM OF GENUS *LACTOBACILLUS*

(71) Applicant: FUJIFILM Corporation, Tokyo (JP)

(72) Inventors: Fumitaka Ueda, Ashigarakami-gun (JP); Yuriko Oda, Ashigarakami-gun (JP); Akihito Amao, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 83 days.

(21) Appl. No.: 16/290,538

(22) Filed: Mar. 1, 2019

(65) Prior Publication Data
US 2019/0192600 A1    Jun. 27, 2019

Related U.S. Application Data

(63) Continuation of application No. PCT/JP2017/031578, filed on Sep. 1, 2017.

(30) Foreign Application Priority Data

Sep. 2, 2016 (JP) .............. JP2016-171497

(51) Int. Cl.
*A61K 36/37* (2006.01)
*A23K 10/30* (2016.01)
*A23K 50/20* (2016.01)
*A23K 50/30* (2016.01)
*A23K 50/10* (2016.01)
*A61P 1/14* (2006.01)
*A61K 36/185* (2006.01)

(52) U.S. Cl.
CPC .............. *A61K 36/37* (2013.01); *A23K 10/30* (2016.05); *A23K 50/10* (2016.05); *A23K 50/20* (2016.05); *A23K 50/30* (2016.05); *A61K 36/185* (2013.01); *A61P 1/14* (2018.01)

(58) Field of Classification Search
None
See application file for complete search history.

(56) References Cited

U.S. PATENT DOCUMENTS

| 2005/0164368 | A1 | 7/2005 | Ji et al. | |
| 2008/0067632 | A1* | 3/2008 | Yamaguchi et al. | A23K 1/16 |
| 2010/0247501 | A1 | 9/2010 | Ikeda | |
| 2010/0261784 | A1 | 10/2010 | Ueda | |
| 2012/0014923 | A1 | 1/2012 | Isa et al. | |
| 2012/0034322 | A1 | 2/2012 | Oda et al. | |
| 2012/0276081 | A1 | 11/2012 | Oda et al. | |
| 2015/0141355 | A1 | 5/2015 | Deshpande et al. | |

FOREIGN PATENT DOCUMENTS

| JP | 2003-235569 A | 8/2003 |
| JP | 2005-102696 A | 4/2005 |
| JP | 2005-323581 A | 11/2005 |
| JP | 2007-31345 A | 2/2007 |
| JP | 2008-67632 A | 3/2008 |
| JP | 2010-248185 A | 11/2010 |
| JP | 5058539 B2 | 10/2012 |
| JP | 2015-127340 A | 7/2015 |
| WO | WO 2009/072674 A1 | 6/2009 |

OTHER PUBLICATIONS

Muraoka et al. (2008) Tetrahedron Letters, 49: 7315-7317. (Year: 2008).*
Australian Office Action for counterpart Australian Application No. 2017319467, dated Jul. 5, 2019.
Extended European Search Report for corresponding European Application No. 17846709.8, dated Sep. 9, 2019.
Flammang et al., "Toxicological and cytogenetic assessment of a Salacia oblonga extract in a rat subchronic study," Food and Chemical Toxicology, vol. 45, No. 10, Aug. 12, 2007, pp. 1954-1962.
Oda et al., "A subchronic oral toxicity study of Salacia reticulata extract powder in rats," Toxicology Reports, vol. 2, Jan. 1, 2015 (published online Jul. 26, 2015), pp. 1136-1144.
Oda et al., "Improvement in Human Immune Function with Changes in Intestinal Microbiota by Salacia reticulata Extract Ingestion: A Randomized Placebo-Controlled Trial," PLOS ONE, vol. 10, No. 12, e0142909, Dec. 2, 2015, pp. 1-13.
Oda et al., "Investigation by Microarray Analysis of the Immunostimulatory Function of an Extract of the Genus Plant *Salacia* in the Small Intestine of Rats," Fujifilm Research and Development, No. 55, 2010, pp. 42-49.
Prasad et al., "Synergistic Antihyperlipidemic Activity of Salacia oblonga, Salaica roxbhurgii and Lagerstroemia parviflora," International Journal of Pharmaceutical Sciences and Drug Research, vol. 9, No. 5, Sep.-Oct. 2017 (Sep. 15, 2017), pp. 280-285, XP055616562.
International Preliminary, Report on Patentability and Written Opinion of the International Searching Authority(Forms PCT/IB/326, PCT/IB/373 and PCT/ISA/237), dated Mar. 14, 2019, for International Application No. PCT/JP2017/031578, with an English Translation of the Written Opinion.
International Search Report, dated Dec. 5, 2017, for International Application No. PCT/JP2017/031578, with an English translation.
(Continued)

*Primary Examiner* — Russell G Fiebig
(74) *Attorney, Agent, or Firm* — Birch, Stewart, Kolasch & Birch, LLP

(57) ABSTRACT

An object of the present invention is to provide a feed for domestic animals or a supplement for domestic animals, a growth-promoting agent for a bacterium of the genus *Lactobacillus*, and a method for promoting growth of a bacterium of the genus *Lactobacillus*, by which an intestinal environment of the domestic animal can be ameliorated without externally administering bacteria, and more specifically, a proportion of bacteria of the genus *Lactobacillus* in intestinal bacteria can be increased. According to the present invention, there is provided a feed for domestic animals or a supplement for domestic animals, which is used for promoting growth of a bacterium of the genus *Lactobacillus* in the domestic animal, the feed or the supplement including (Continued)

at least one of a plant of the genus *Salacia*, an extract of the plant of the genus *Salacia*, or a ground product of the plant of the genus *Salacia*.

9 Claims, No Drawings

(56) References Cited

OTHER PUBLICATIONS

European Office Action, dated Apr. 14, 2020 for corresponding European Application No. 17846709.8.
Australian Office Action dated Apr. 20, 2020, for corresponding Australian Patent Application No. 2017319467.
New Zealand Office Action dated Sep. 25, 2020 for Corresponding Application No. 751143.

\* cited by examiner

FEED FOR DOMESTIC ANIMALS OR SUPPLEMENT FOR DOMESTIC ANIMALS, GROWTH-PROMOTING AGENT FOR BACTERIUM OF GENUS *LACTOBACILLUS*, AND METHOD FOR PROMOTING GROWTH OF BACTERIUM OF GENUS *LACTOBACILLUS*

CROSS-REFERENCE TO RELATED APPLICATIONS

This application is a Continuation of PCT International Application No. PCT/JP2017/031578 filed on Sep. 1, 2017, which claims priority under 35 U.S.C § 119(a) to Japanese Patent Application No. 2016-171497 filed on Sep. 2, 2016. Each of the above application(s) is hereby expressly incorporated by reference, in its entirety, into the present application.

BACKGROUND OF THE INVENTION

1. Field of the Invention

The present invention relates to a feed for domestic animals or a supplement for domestic animals, which contains *Salacia*. The present invention further relates to a growth-promoting agent for a bacterium of the genus *Lactobacillus* in domestic animals, which contains *Salacia*. The present invention further relates to a method for promoting growth of a bacterium of the genus *Lactobacillus* in domestic animals, which includes administering *Salacia*.

2. Description of the Related Art

The Thoroughbred is a light horse breed that has used the Arabian horse, a hunter type (a breed used for hunting originated in English), and the like to improve breed thereof as a racehorse in the early 18th-century England. The Thoroughbred is repeatedly crossed and selected aiming to win at horse racing still in present time. The Thoroughbred can run at speeds of 60 to 70 km/hour for several minutes continuously while being in a state of carrying weights of 48 to 59 kg on the back when racing. The Thoroughbred is a high added-value industrial animal, and about 110,000 kinds thereof are produced all around the world, including the United States, Australia, Ireland, Japan, and the like every year.

Examples of diseases of the Thoroughbred include diarrhea in addition to muscle fatigue, arthritis pain, trauma and bone fracture, and the like caused by training, race, and the like. Examples of the diarrhea in the Thoroughbred include foal diarrhea induced by rotavirus infection, diarrhea induced by administration of an antimicrobial agent to treat diseases or for transportation, diarrhea induced by colitis-X having a high mortality rate, and the like. The diarrhea in the Thoroughbred is a serious disease directly connected to a price decline due to inhibition of foal growth, and the performance and life and death of active horses, and therefore normalization of the intestinal environment has been demanded for the purpose of ameliorating such a diarrhea in the Thoroughbred.

As a method for increasing good bacteria in the intestine for the purpose of ameliorating such intestinal environment, a method of allowing an animal to ingest lactic acid bacteria or *Lactobacillus bifidus* is known. JP2003-235569A discloses a feed additive containing a culture of a microorganism belonging to the genus *Lactobacillus* having predetermined chemotaxonomic properties and/or a microbial cell as an active ingredient. JP2005-102696A discloses a product for intestinal disorders, which contains a novel strain of *Bifidobacterium longum* having inhibitory activity against rotavirus known to cause diarrhea in children and young animals, as an active ingredient.

Meanwhile, the roots and stems of a plant of the genus *Salacia* (also called Kota Rahim) have been used as natural drugs in traditional medicine Ayurveda in India and Sri Lanka. In Sri Lanka, it has been passed down that the root skin of *Salacia reticulata* is effective for treatment of rheumatism, gonorrhea, and skin diseases, and that the root skin is used for treatment of diabetes in early stage. JP2008-067632A discloses a supplement for animals, which includes royal jelly, Kota Rahim, and coenzyme Q10. In addition, JP2010-248185A discloses a promoter of hypoglycemia action by an α-glucosidase inhibitor, which includes at least one kind of bacteria selected from the group consisting of *Lactobacillus bifidus*, lactic acid bacteria, saccharified bacteria, and butyric acid bacteria. JP2010-248185A discloses that *Salacia* may be used as an α-glucosidase inhibitor.

SUMMARY OF THE INVENTION

The inventors of the present invention have studied for the purpose of normalizing the intestinal environment of a domestic animal such as a horse represented by Thoroughbred, and have found that effects were insufficient in all cases. For example, in the feed additive disclosed in JP2003-235569A, lactic acid bacteria themselves are administered to an animal, and therefore it is necessary to enhance the stability of the lactic acid bacteria themselves, and furthermore, the effect was not obtained depending on the predisposition of the animal to be administered. In addition, the product for intestinal disorders disclosed in JP2005-102696A uses *Lactobacillus bifidus*, but in a case where the product is administered to a horse, an intestinal pH excessively decreases, and therefore there was a concern that an environment becomes an internal environment not preferable for the growth environment of lactic acid bacteria. In particular, in the method of allowing an animal to ingest lactic acid bacteria or *Lactobacillus bifidus* themselves as in JP2003-235569A and JP2005-102696A, there was a problem that the number of viable bacteria decreases during a storage period before ingestion, or ingested bacteria are sterilized in a case of, for example, passing through the acidic environment of the stomach, and therefore the effect is insufficiently exhibited.

In the supplement for animals disclosed in JP2008-067632A, the royal jelly is the main component, and the intestinal environment has not been examined. In addition, in the promoter of hypoglycemia action disclosed in JP2010-248185A, at least one kind of bacteria itself selected from the group consisting of *Lactobacillus bifidus*, lactic acid bacteria, saccharified bacteria, and butyric acid bacteria is used, but the intestinal environment has not been examined.

The problem to be solved by the present invention is to provide a feed for domestic animals or a supplement for domestic animals, a growth-promoting agent for a bacterium of the genus *Lactobacillus*, and a method for promoting growth of a bacterium of the genus *Lactobacillus*, by which an intestinal environment of the domestic animal can be ameliorated without externally administering bacteria, and more specifically, a proportion of bacteria of the genus *Lactobacillus* in intestinal bacteria can be increased.

As a result of intensive studies to solve the above problems, the inventors of the present invention have found that the number of bacteria of the genus *Lactobacillus* can be greatly increased without externally administering bacteria by allowing the domestic animal to ingest *Salacia*, and therefore have completed the present invention. According to the present invention, the following invention is provided.

[1] A feed for domestic animals or a supplement for domestic animals, which is used for promoting growth of a bacterium of the genus *Lactobacillus* in the domestic animal, the feed or the supplement comprising: at least one of a plant of the genus *Salacia*, an extract of the plant of the genus *Salacia*, or a ground product of the plant of the genus *Salacia*.

[2] The feed for domestic animals or the supplement for domestic animals according to [1], in which an average pH of feces after ingestion for 6 days is 6.0 to 8.2.

[3] The feed for domestic animals or the supplement for domestic animals according to [1] or [2], in which an amount of acetic acid in feces after ingestion for 6 days is increased by 1.1 times or more as compared to an amount of acetic acid in feces before ingestion.

[4] The feed for domestic animals or the supplement for domestic animals according to any one of [1] to [3], in which the bacterium of the genus *Lactobacillus* is at least one selected from the group consisting of *Lactobacillus* equi, *Lactobacillus* hayakitensis, *Lactobacillus* equigenerosi, *Lactobacillus* delbrueckii, and *Lactobacillus* ingluviei.

[5] A growth-promoting agent for a bacterium of the genus *Lactobacillus* in domestic animals, comprising: at least one of a plant of the genus *Salacia*, an extract of the plant of the genus *Salacia*, or a ground product of the plant of the genus *Salacia*.

[6] The growth-promoting agent for a bacterium of the genus *Lactobacillus* in domestic animals according to [5], in which an average pH of feces after ingestion for 6 days is 6.0 to 8.2.

[7] The growth-promoting agent for a bacterium of the genus *Lactobacillus* in domestic animals according to [5] or [6], in which an amount of acetic acid in feces after ingestion for 6 days is increased by 1.1 times or more as compared to an amount of acetic acid in feces before ingestion.

[8] The growth-promoting agent for a bacterium of the genus *Lactobacillus* in domestic animals according to any one of [5] to [7], in which the bacterium of the genus *Lactobacillus* is at least one selected from the group consisting of *Lactobacillus* equi, *Lactobacillus* hayakitensis, *Lactobacillus* equigenerosi, *Lactobacillus* delbrueckii, and *Lactobacillus* ingluviei.

[9] A method for promoting growth of a bacterium of the genus *Lactobacillus* in domestic animals, comprising: administering at least one of a plant of the genus *Salacia*, an extract of the plant of the genus *Salacia*, or a ground product of the plant of the genus *Salacia* to the domestic animal.

[10] The method according to [9], in which an average pH of feces after ingestion for 6 days is 6.0 to 8.2.

[11] The method according to [9] or [10], in which an amount of acetic acid in feces after ingestion for 6 days is increased by 1.1 times or more as compared to an amount of acetic acid in feces before ingestion.

[12] The method according to any one of [9] to [11], in which the bacterium of the genus *Lactobacillus* is at least one selected from the group consisting of *Lactobacillus* equi, *Lactobacillus* hayakitensis, *Lactobacillus* equigenerosi, *Lactobacillus* delbrueckii, and *Lactobacillus* ingluviei.

According to the feed for domestic animals or the supplement for domestic animals, the growth-promoting agent for a bacterium of the genus *Lactobacillus*, and the method for promoting growth of a bacterium of the genus *Lactobacillus* according to the embodiment of the invention, the number of bacteria of the genus *Lactobacillus* can be greatly increased without externally administering bacteria.

DESCRIPTION OF THE PREFERRED EMBODIMENTS

Hereinafter, embodiments of the present invention will be described.

A feed for domestic animals or a supplement for domestic animals according to the embodiment of the invention, and a growth-promoting agent for a bacterium of the genus *Lactobacillus* in domestic animals according to the embodiment of the invention contain at least one of a plant of the genus *Salacia*, an extract of the plant of the genus *Salacia*, or a ground product of the plant of the genus *Salacia*.

Generally, it is known that, in a case where a human ingests *Salacia*, there is a tendency that a weight gain is suppressed or a body weight decreased due to the following reasons. First, in a case where a human ingests *Salacia*, *Lactobacillus bifidus* mainly increases in the intestine. This *Lactobacillus bifidus* breaks down sugar and produces lactic acid and acetic acid, which are energy sources more easily consumable than sugar. In addition, it is known that *Salacia* has an inhibitory action on α-glucosidase, an enzyme that degrades polysaccharides. For this reason, it is known that an effect of suppression of blood sugar elevation and an anti-obesity effect are obtained by *Salacia* ingestion in humans.

With respect to the above description, the inventors of the present invention have conducted the investigation and confirmed that a body weight increases in a case where a non-human animal ingests *Salacia*. In more detail, the inventors of the present invention have found by the present investigation that the bacteria of the genus *Lactobacillus*, which are a kind of lactic acid bacteria, increase in the intestine.

Regarding the above viewpoint, the inventors of the present invention presume as follows.

It is considered that, in the case where the non-human animal ingests *Salacia*, the polysaccharide reaches the large intestine in a form of disaccharide or oligosaccharide, and these saccharides are degraded by bacteria in the large intestine, but the non-human animal does not have *Lactobacillus bifidus*, and therefore a lactic acid bacteria group increases and thus the intestinal environment is normalized. Regarding the above viewpoint, the inventors of the present invention have further conducted investigation in detail. As a result, in the case where the non-human animal ingested *Salacia*, the bacteria of the genus *Lactobacillus*, which are bacteria classified as Firmicutese as good bacteria, remarkably increased. It is presumed that by the increase of bacteria of the genus *Lactobacillus*, lactic acid and acetic acid are produced and thus energy metabolism is enhanced, and in addition, these acids degrade dietary fibers and the like which are not originally absorbed as nutrients, and change the dietary fibers into a state capable of being absorbed as nutrients, leading to a weight gain. That is, it is considered that, in the case where the non-human animal ingested *Salacia*, the amelioration of the intestinal environment raises an energy recovery rate from the meal and makes fat to be easily stored, and as a result, an increase in a body weight is confirmed. In addition, as described above, since lactic acid and acetic acid are energy sources which are easily consumed, it is considered that the energy sources also increase by the increase of bacterium of the genus *Lactobacillus*, and therefore stamina of the non-human animal that has ingested *Salacia* increases.

As described above, the effect of *Salacia* is greatly different between humans and non-human animals. In a case where the domestic animal such as a horse ingests *Salacia*, the bacteria of the genus *Lactobacillus* in the intestine can be increased without externally administering bacteria. That is, the finding that the growth of bacteria of the genus *Lactobacillus* originally contained in the domestic animal is promoted is absolutely unexpected. A proportion of *Lactobacillus bifidus* in the intestine in humans is about 20% at maximum, whereas *Lactobacillus bifidus* is not detected in horses, and therefore a proportion of *Lactobacillus bifidus* and lactic acid bacteria in the intestinal bacteria is significantly different in human and horses. Accordingly, in a case where the human or non-human animal ingest bacteria themselves, the type of bacteria to be ingested should be originally different for both cases, but studies thereon have not been made sufficiently in the related art. As described above, the composition of the intestinal bacteria is different between humans and horses, and therefore it is difficult to predict an effect of *Salacia* ingestion in the non-human animals such as domestic animals.

<Domestic Animal>

The domestic animal generally means mammals and birds other than humans, which are raised by humans. Examples of the domestic animal in the present invention include domestic animals excluding birds and pets, and specific examples thereof include horse (light horse breed, intermediate horse breed, and heavy horse breed), pig, cow (dairy cattle, beef cattle), sheep, goat, and the like. The domestic animal is preferably herbivores.

The domestic animal in the present invention is preferably a horse and more preferably the light horse breed. The light horse breed is the type of horse, generally means Arab, Thoroughbred, Anglo-Arab, Arabic types, and Thoroughbred types. The domestic animal in the present invention is particularly preferably the Thoroughbred. A horse such as the Thoroughbred may not only be a racehorse but also be a young horse still being raised, a horse for horse riding after retirement, or a horse for meat.

<Plant of Genus *Salacia*, Extract of Plant of Genus *Salacia*, and Ground Product of Plant of Genus *Salacia*>

The plant of the genus *Salacia* is a plant of the family Hippocrateaceae, which grows primarily in Sri Lanka, India, and Southeast Asia. Specific examples of the plant of the genus *Salacia* include one or more plants selected from *Salacia reticulata, Salacia oblonga, Salacia prinoides, Salacia chinensis, Salacia latifolia, Salacia burunoniana, Salacia grandiflora*, or *Salacia macrosperma*. As the plant of the genus *Salacia*, at least one plant selected from *Salacia reticulata, Salacia oblonga*, or *Salacia chinensis* is preferable.

In the present invention, at least one of the plant of the genus *Salacia*, the extract of the plant of the genus *Salacia*, or the ground product of the plant of the genus *Salacia* may be used, and the plant of the genus *Salacia* can be preferably used. As the plant of the genus *Salacia*, edible parts such as roots, stems, leaves, flowers, and fruits of the plant of the genus *Salacia* can be used as they are.

In the present specification, the term extract of the plant of the genus *Salacia* and the term ground product of the plant of the genus *Salacia* are used to include an extract and/or a ground product of the edible parts such as roots, stems, leaves, flowers, and fruits of the plant of the genus *Salacia*, and a dried product of the extract and/or the ground product. In the present specification, the dried product may be a dry powder (extract powder). In a case of preparing the extract and/or the ground product of the plant of the genus *Salacia*, a part of one or more kinds of the plants of the genus *Salacia* may be mixed and used. From the viewpoint of enhancing intake efficiency of the domestic animal, as the extract of the plant of the genus *Salacia*, an extract powder obtained by drying the extract extracted from a part selected from the root and the stem is more preferably used.

The dry powder (extract powder) can be preferably obtained by extracting the edible parts and the like of the plant of the genus *Salacia* with a solvent and then drying the extract obtained above. Examples of the solvent used for the extraction include water, alcohol, ketone, and the like, and a mixed solvent in which two or more kinds thereof are mixed may be used. Examples of the alcohol include methanol, ethanol, and the like, and ethanol is preferable. Preferred examples of the ketone include acetone, methyl ethyl ketone, cyclohexane, and the like.

Among the above examples, water, alcohol, a mixed solvent of water and alcohol, or a mixed solvent of water and ketone is preferable, water, alcohol, or a mixed solvent of water and alcohol is more preferable, and hot water at 50° C. to 98° C., ethanol, or a mixed solvent of water and ethanol is even more preferable.

A content of alcohol in the mixed solvent of water and alcohol is preferably from 30% by mass to 90% by mass, and more preferably from 40% by mass to 70% by mass. A drying method for drying the extract so as to obtain the dry powder (extract powder) is not particularly limited, and examples thereof include known drying methods such as spray drying and freeze-drying.

<Feed for Domestic Animals or Supplement for Domestic Animals>

According to a first aspect of the present invention, there is provided the feed for domestic animals or the supplement for domestic animals, which contains at least one of the plant of the genus *Salacia*, the extract of the plant of the genus *Salacia*, or the ground product of the plant of the genus *Salacia*. The feed for domestic animals or the supplement for domestic animals according to the embodiment of the invention is used for promoting the growth of the bacteria of the genus *Lactobacillus* in the domestic animal. The bacteria of the genus *Lactobacillus* will be described later in the present specification.

The feed for domestic animals according to the embodiment of the invention can be produced by formulating at least one of the plant of the genus *Salacia*, the extract of the plant of the genus *Salacia*, or the ground product of the plant of the genus *Salacia*, into a basic feed generally used according to the type of domestic animals.

The basic feed may be any feed that has been supplied to each domestic animal in the related art. In a case of a horse such as a racehorse, examples of the basic feed include pasture grasses, cereals such as oats, beans (soybeans and the like), oil meal, and the like, but are not particularly limited. It is also possible to use a formulated feed in which a plurality of ingredients are formulated.

As the formulated feed, for example, formulated feeds shown below can be used.

A feed in which oats, fusuma, corn, soybean cake, barley, alfalfa, vitamins, and minerals are formulated;

A feed in which vitamins, minerals, herbs, and the like are formulated with oats, fusuma, alfalfa meal, corn, wheat flour, corn gluten feed, and soybean oil meal as main ingredients;

A feed in which vitamins, minerals, herbs, and the like are formulated with corn, barley, oats, wheat flour, soybean, fusuma, soybean cake, rapeseed oil cake, molasses, and vegetable oil as main ingredients;

A feed in which coenzyme Q10, carnosine, and soybean peptide are formulated with oats, fusuma, barley, corn, wheat flour, soybean oil meal, soybean, molasses, vitamins and minerals, herbs, and the like as usual ingredients;

A feed in which vitamins, minerals, herbs, and the like are formulated with corn, barley, wheat flour, soybean, rice bran, fusuma, soybean cake, rapeseed oil cake, black sunflower, molasses, and vegetable oil as main ingredients;

A feed in which proteins, vitamins, and minerals are formulated with soybean, black sunflower, soybean cake, corn gluten meal, molasses, corn, and beet pulp as main ingredients, feeding being in the premise that the feed is mixed with oats and then supplied; and A feed in which corn, barley, heat-treated soybean, black sunflower seed, oats, soybean cake, rapeseed cake, beet pulp, and the like are formulated.

The feed for domestic animals according to the embodiment of the invention may contain additives such as a reinforcing agent, a quality improver, an antibiotic, an antimicrobial agent, an enzyme, an antibacterial agent, an antioxidant, a colorant, a sweetener, and a perfume.

A content of "at least one of the plant of the genus *Salacia*, the extract of the plant of the genus *Salacia*, or the ground product of the plant of the genus *Salacia*" in the feed for domestic animals according to the embodiment of the invention is not particularly limited, but is generally from 1% by mass to 50% by mass, preferably from 2% by mass to 40% by mass, more preferably from 3% by mass to 30% by mass, and even more preferably from 5% by mass to 20% by mass.

The supplement for domestic animals is a supplement which is added to a feed for the domestic animal and then fed together with the feed for the purpose of maintaining, restoring, or promoting health, or preventing or ameliorating diseases, and the like. The supplement for domestic animals according to the embodiment of the invention is particularly preferably a supplement for a racehorse (Thoroughbred).

As the supplement for domestic animals according to the embodiment of the invention, at least one of the plant of the genus *Salacia*, the extract of the plant of the genus *Salacia*, or the ground product of the plant of the genus *Salacia* itself may be used alone, or an supplement in which at least one of the plant of the genus *Salacia*, the extract of the plant of the genus *Salacia*, or the ground product of the plant of the genus *Salacia* is formulated with other components may be used.

Examples of the other components include mineral yeast, flavonoid, polyphenol, oral substances having an immunopotentiation action, and the like, and are not particularly limited. Specific examples of the other components include the components described in paragraphs 0023 to 0038 of JP2015-127340A.

The supplement for domestic animals according to the embodiment of the invention may further contain one or more selected from vitamins, vitamin-like substances, proteins, amino acids, oils and fats, organic acids, carbohydrates, plant-derived raw materials, animal-derived raw materials, food additives, and pharmaceutical additives, and the like, which are orally ingestible components, as appropriate.

The supplement for domestic animals according to the embodiment of the invention can be prepared by using various carriers, for example, one or more additives selected from excipients, lubricants, stabilizers, dispersants, binders, diluents, flavoring agents, sweeteners, flavorings, and colorants, may preferably be prepared as an orally administered agent.

A form of the supplement for domestic animals according to the embodiment of the invention is not particularly limited as long as the effect of the present invention can be exhibited. For example, the form may be a form such as tablets, pills, granules, fine granules, peptizers, capsules (hard capsules or soft capsules filled with the supplement), liquid drug, and chewable agents.

A content of "at least one of the plant of the genus *Salacia*, the extract of the plant of the genus *Salacia*, or the ground product of the plant of the genus *Salacia*" in the supplement for domestic animals according to the embodiment of the invention is not particularly limited, but is generally from 10% by mass to 100% by mass, preferably from 20% by mass to 100% by mass, more preferably from 50% by mass to 100% by mass, even more preferably from 70% by mass to 100% by mass, particularly preferably from 90% by mass to 100% by mass, and most preferably 100% by mass. That is, it is most preferable to use "at least one of the plant of the genus *Salacia*, the extract of the plant of the genus *Salacia*, or the ground product of the plant of the genus *Salacia*" as it is as the supplement for domestic animals according to the embodiment of the invention.

<Growth-Promoting Agent for Bacterium of the Genus *Lactobacillus* in Domestic Animals>

According to a second aspect of the present invention, there is provided a growth-promoting agent for a bacterium of the genus *Lactobacillus* in domestic animals, including at least one of a plant of the genus *Salacia*, an extract of the plant of the genus *Salacia*, or a ground product of the plant of the genus *Salacia*.

The bacteria of the genus *Lactobacillus* are gram positive bacteria classified as lactic acid bacteria. The genus *Lactobacillus* is the largest genus among about 30 lactic acid bacteria. The bacteria of the genus *Lactobacillus* are widely distributed in nature, and there are over 70 types of bacteria of the genus *Lactobacillus*.

The bacteria of the genus *Lactobacillus* are preferably bacteria present in the intestines of horses.

The bacteria of the genus *Lactobacillus* are more preferably bacteria present in the intestine of the horse and are bacteria not present in the human intestine.

The bacterium of the genus *Lactobacillus* is more preferably at least one selected from the group consisting of *Lactobacillus* equi, *Lactobacillus* hayakitensis, *Lactobacillus* equigenerosi, *Lactobacillus* delbrueckii, and *Lactobacillus* ingluviei.

Whether or not the growth-promoting agent for a bacterium of the genus *Lactobacillus* in domestic animals according to the embodiment of the invention can promote the growth of the bacteria of the genus *Lactobacillus* bacteria can be confirmed by the following method, for example.

A predetermined amount of the growth-promoting agent for a bacterium of the genus *Lactobacillus* in domestic animals according to the embodiment of the invention is allowed to be ingested by the domestic animal for a certain period of time, and feces before and after the ingestion period is collected. DNA is extracted from the collected feces, and a sequence library is prepared using the obtained DNA. Sequence is performed by next generation sequencer (MiSeq; Illumina), data with high similarity is divided into groups (Operation Taxonomic Unit (OTU)), and lineage classification is estimated. The number of sequence data belonging to each classification group is tabulated and comparison of data before and after is performed. However, an abundance ratio differs greatly for each bacterium, and therefore an initial value is set to 100, comparison of the number of bacteria before ingestion and after the ingestion is carried out. With the value becoming less than 100 after ingestion, it can be confirmed whether or not the above-described predetermined number of bacteria can be suppressed.

As the growth-promoting agent for a bacterium of the genus *Lactobacillus* in domestic animals according to the embodiment of the invention, at least one of the plant of the genus *Salacia*, the extract of the plant of the genus *Salacia*, or the ground product of the plant of the genus *Salacia* itself may be used alone, or an supplement in which at least one of the plant of the genus *Salacia*, the extract of the plant of the genus *Salacia*, or the ground product of the plant of the genus *Salacia* is formulated with other components may be used.

Examples of the other components include mineral yeast, flavonoid, polyphenol, oral substances having an immunopotentiation action, and the like, and are not particularly limited. Specific examples of the other components include the components described in paragraphs 0023 to 0038 of JP2015-127340A.

The growth-promoting agent for a bacterium of the genus *Lactobacillus* in domestic animals according to the embodiment of the invention may further contain one or more selected from vitamins, vitamin-like substances, proteins, amino acids, oils and fats, organic acids, carbohydrates, plant-derived raw materials, animal-derived raw materials, feed additives, and pharmaceutical additives for animals, and the like, which are orally ingestible components, as appropriate.

The growth-promoting agent for a bacterium of the genus *Lactobacillus* in domestic animals according to the embodiment of the invention can be prepared by using various carriers, for example, one or more additives selected from excipients, lubricants, stabilizers, dispersants, binders, diluents, flavoring agents, sweeteners, flavorings, and colorants, may preferably be prepared as an orally administered agent.

A form the growth-promoting agent for a bacterium of the genus *Lactobacillus* in domestic animals according to the embodiment of the invention is not particularly limited as long as the effect of the present invention can be exhibited. For example, the form may be a form such as tablets, pills, granules, fine granules, peptizers, capsules (hard capsules or soft capsules filled with the supplement), liquid drug, and chewable agents.

A content of "at least one of the plant of the genus *Salacia*, the extract of the plant of the genus *Salacia*, or the ground product of the plant of the genus *Salacia*" in the growth-promoting agent for a bacterium of the genus *Lactobacillus* in domestic animals according to the embodiment of the invention is not particularly limited, but is generally from 10% by mass to 100% by mass, preferably from 20% by mass to 100% by mass, more preferably from 50% by mass to 100% by mass, even more preferably from 70% by mass to 100% by mass, particularly preferably from 90% by mass to 100% by mass, and most preferably 100% by mass. That is, it is most preferable to use "at least one of the plant of the genus *Salacia*, the extract of the plant of the genus *Salacia*, or the ground product of the plant of the genus *Salacia*" as it is as the growth-promoting agent for a bacterium of the genus *Lactobacillus* in domestic animals according to the embodiment of the invention.

<Method for Promoting Growth of Bacterium of the Genus *Lactobacillus* in Domestic Animals>

The feed for domestic animals or the supplement for domestic animals, and the growth-promoting agent for a bacterium of the genus *Lactobacillus* according to the embodiment of the invention have the domestic animal as an administration subject, and can be orally administered to the domestic animal.

That is, according to a third aspect of the present invention, there is provided a method for promoting growth of a bacterium of the genus *Lactobacillus* in domestic animals, including: administering at least one of a plant of the genus *Salacia*, an extract of the plant of the genus *Salacia*, or a ground product of the plant of the genus *Salacia* to the domestic animal.

The bacterium of the genus *Lactobacillus* and preferred ranges thereof are as described above in the present specification.

The method for administering at least one of the plant of the genus *Salacia*, the extract of the plant of the genus *Salacia*, or the ground product of the plant of the genus *Salacia* to the domestic animal is not particularly limited, but oral administration, that is, the domestic animal may orally ingest at least one thereof.

In a case where an inhibitor of the number of enteric bacteria of the feed for domestic animals or the supplement for domestic animals, or the growth-promoting agent for a bacterium of the genus *Lactobacillus* according to the embodiment of the invention is administered to the domestic animal, a daily intake amount or a dose of "at least one of the plant of the genus *Salacia*, the extract of the plant of the genus *Salacia*, or the ground product of the plant of the genus *Salacia*" is preferably 0.1 mg/kg/day or more, more preferably 0.5 mg/kg/day or more, even more preferably 1.0 mg/kg/day or more, still even more preferably 2.0 mg/kg/day or more, and particularly preferably 4.0 mg/kg/day or more. An upper limit of a daily intake amount or a dose of the extract and/or the ground product of the plant of the genus *Salacia* is not particularly limited, but is generally 2000 mg/kg/day or less, and preferably 1000 mg/kg/day or less.

In a case where the inhibitor of the number of enteric bacteria of the feed for domestic animals or the supplement for domestic animals, or the growth-promoting agent for a bacterium of the genus *Lactobacillus* according to the embodiment of the invention is administered to the domestic animal, the number of bacteria of the genus *Lactobacillus* preferably increases by 1.1 times or more, more preferably 1.5 times or more, even more preferably 2 times or more, still even more preferably 5 times or more, and particularly preferably 10 times or more. At this time, increasing bacteria of the genus *Lactobacillus* are preferably at least one kind selected from group consisting of *Lactobacillus* equi, *Lactobacillus* hayakitensis, *Lactobacillus* equigenerosi, *Lactobacillus* delbrueckii, and *Lactobacillus* ingluviei, and most preferably contain *Lactobacillus* equi.

<Regarding Average pH of Feces after Ingestion for 6 Days>

An average pH of feces after ingestion of the feed for domestic animals or the supplement for domestic animals or the growth-promoting agent for a bacterium of the genus *Lactobacillus* according to the embodiment of the invention for 6 days is not particularly limited, but is preferably from 6.0 to 8.2, more preferably from 6.5 to 8.2, even more preferably from 7.0 to 8.2, still even more preferably from 7.4 to 8.2, and particularly preferably from 7.6 to 8.0. By setting the average pH of feces within the above range, it is possible to suppress the effect of killing cellulose-degrading bacteria, to suppress the increase of bad bacteria, and to maintain good intestinal environment.

The average pH of feces can be measured by the following method. A certain amount of the feces is weighed out and a sample solution is prepared by adding 9 times an amount of purified water to the mass thereof. The obtained sample solution is thoroughly shaken and the sample is dispersed in purified water. Subsequently, after the sample solution is heated at 80° C. for 30 minutes to inactivate virus and the like contained in the sample, the sample solution is left to stand. After allowing the sample solution to stand still, the supernatant of the sample solution is collected and pH measurement is performed with the glass electrode. For the pH measurement, a compact pH meter (LAQUAtwin B-172, manufactured by Horiba Seisakusho Co., Ltd.) can be used.

<Regarding Acetic Acid>

According to the feed for domestic animals or the supplement for domestic animals, the growth-promoting agent for a bacterium of the genus *Lactobacillus*, and the method for promoting growth of a bacterium of the genus *Lactobacillus* according to the embodiment of the invention, an amount of acetic acid in the feces can be preferably increased. The acetic acid can ameliorate the intestinal environment by promoting intestinal peristaltic movement. The amount of acetic acid in the feces after ingestion for 6 days preferably increased by 1.1 times or more, more preferably 1.2 times or more, even more preferably 1.3 times or more, still even more preferably 1.4 times or more, and particularly preferably 1.5 times or more, as compared with an amount of acetic acid in feces before ingestion.

The amount of acetic acid in the feces can be measured by general methods. Examples of the method include a method described in the examples below.

<Regarding Bacteria of Genus *Clostridium*>

According to the feed for domestic animals or the supplement for domestic animals, the growth-promoting agent for a bacterium of the genus *Lactobacillus*, and the method for promoting growth of a bacterium of the genus *Lactobacillus* according to the embodiment of the invention, the number and/or a proportion of bacteria of the genus *Clostridium* in the intestinal bacteria can be preferably lowered. By ingestion of the feed for domestic animals or the supplement for domestic animals or the growth-promoting agent for a bacterium of the genus *Lactobacillus* according to the embodiment of the invention, the number of bacteria of the genus *Clostridium* is preferably lowered by 0.9 times or less, more preferably 0.8 times less, even more preferably 0.7 times or less, and particularly preferably 0.6 times or less, as compared with the number of bacteria before ingestion.

The bacteria of the genus *Clostridium* are obligate anaerobic bacteria that live in low oxygen concentration environments such as in the soil and in the intestine of organisms and cannot grow in the presence of oxygen. A large number of pathogenic bacteria are also contained in the bacteria of the genus *Clostridium*, and therefore, adverse effects caused by pathogenic bacteria can be suppressed in some cases according to the present invention.

The measurement of whether the number or a proportion of the bacteria of the genus *Clostridium* is lowered or not can be carried out in the same manner as the method for measuring whether the growth of the bacteria of the genus *Lactobacillus* can be promoted or not.

<Application of Plant of Genus *Salacia*, Extract of Plant of Genus *Salacia*, and Ground Product of Plant of Genus *Salacia*>

Furthermore, according to the present invention, at least one of the plant of the genus *Salacia*, the extract of the plant of the genus *Salacia*, or the ground product of the plant of the genus *Salacia*, which is used in raising of the domestic animal, which includes administration of the feed or the supplement used for promoting the growth of the bacteria of the genus *Lactobacillus* in the domestic animal, is provided.

Furthermore, according to the present invention, at least one of the plant of the genus *Salacia*, the extract of the plant of the genus *Salacia*, or the ground product of the plant of the genus *Salacia*, which is used in procedure for promoting the growth of the bacteria of the genus *Lactobacillus* in the domestic animal, is provided.

Furthermore, according to the present invention, use of at least one of the plant of the genus *Salacia*, the extract of the plant of the genus *Salacia*, or the ground product of the plant of the genus *Salacia*, which is for producing the feed for domestic animals or the supplement for domestic animals used for promoting the growth of the bacteria of the genus *Lactobacillus* in the domestic animal, is provided.

Furthermore, according to the present invention, use of at least one of the plant of the genus *Salacia*, the extract of the plant of the genus *Salacia*, or the ground product of the plant of the genus *Salacia*, which is for producing the growth-promoting agent for a bacterium of the genus *Lactobacillus* in domestic animals, is provided.

Preferred aspects of each invention described above are as described above in the present specification.

EXAMPLES

Hereinafter, the present invention will be more specifically described based on the following examples, but the present invention is not limited to the following examples. In the present specification, "Tris" is an abbreviation for trishydroxymethylaminomethane, and "EDTA" is an abbreviation for ethylenediaminetetraacetic acid.

Example 1

Root and stem parts of *Salacia reticulata* and *Salacia oblonga* were ground, and then mixed in equal weight. A solution obtained through a hot water extraction step at 98° C. was spray dried, and therefore *Salacia* extract powder was obtained.

Example 2

<Changes in the Number of Bacteria of the Genus *Lactobacillus* and Bacteria of the Genus *Clostridium* in Feces>

12 Thoroughbreds aged 2 to 12 years old (weight: 440 to 480 kg) ingested 9 g of the *Salacia* extract powder per day. The changes in the number of bacteria of the genus *Lactobacillus* and bacteria of the genus *Clostridium* in feces before the ingestion of the *Salacia* extract powder and after the ingestion of the *Salacia* extract powder for 6 days were measured by T-RFLP (Nagashima method). In Terminal Restriction Fragment Length Polymorphism (T-RFLP) analysis, template DNA was amplified by polymerase chain reaction (PCR) with a terminal fluorescence-labeled primer set, and after digestion with a restriction enzyme, fragment analysis was performed. The T-RFLP analysis is a fragment polymorphism analysis for evaluation and comparison based on the intensity, position, and the number of detected peaks by using that restriction enzyme cleavage sites differs due to a difference in DNA base sequence. The number of bacteria in the feces can be stored in the database according to the "Nagashima method," intestinal bacteria are estimated at a genus level, and a change can be visualized and quantified.

The results are shown in Table 1.

Numerical values in the table indicate relative values when the number of bacteria before ingestion of the *Salacia* extract powder is taken as 100.

TABLE 1

|  | Bacteria of the genus *Lactobacillus* | Bacteria of the genus *Clostridium* |
|---|---|---|
| Before ingestion of *Salacia* extract powder | 100 | 100 |
| After ingestion of *Salacia* extract powder for 6 days | 1170 | 60 |

As shown in Table 1, the proportion of the bacteria of the genus *Lactobacillus*, which are good bacteria, was significantly increased by ingestion of the *Salacia* extract powder, and the proportion of the bacteria of the genus *Clostridium* to which many pathogenic bacteria belong to was lowered.

<Changes in Average pH of Feces and Amount of Acetic Acid in Feces>

In addition, the average pH of feces and the amount of acetic acid in feces were measured before ingestion of the *Salacia* extract powder and after ingestion of the *Salacia* extract powder for 6 days.

The average pH of feces was measured by the following method. A certain amount of the sample (feces) was weighed out and a sample solution was prepared by adding 9 times an amount of purified water to the mass thereof. The obtained sample solution was thoroughly shaken, and the sample was dispersed in purified water. Subsequently, after the sample solution was heated at 80° C. for 30 minutes to inactivate virus and the like contained in the sample, the sample solution was left to stand. After allowing the sample solution to stand still, the supernatant of the sample solution was collected and pH measurement was performed with the glass electrode. For the pH measurement, a compact pH meter (LAQUAtwin B-172, manufactured by Horiba Seisakusho Co., Ltd.) was used.

The amount of acetic acid in feces was measured by the following method.

The certain amount of the sample (feces) was precisely weighed in a bead tube, and suspended with an extraction solution, and therefore a sample solution was obtained. Subsequently, the obtained sample solution was heat-treated (at 85° C. for 20 minutes), the sample was grounded by physical pulverization (beads and shaking), and centrifugation (14000 rpm, 10 minutes) was carried out. The supernatant of the sample solution was collected and filtered through a membrane filter having a pore size of 0.45 µm, and a solution thus obtained was used as a solution for measurement.

A concentration of acetic acid contained in the sample for measurement was measured by high performance liquid chromatography, and was converted into the amount of acetic acid in the sample.

The extraction solution is not particularly limited as long as it is a solution containing water, but a p-toluenesulfonic acid solution is preferable.

The results are shown in Table 2. Numerical values of the amount of acetic acid in feces in the table indicate relative values when the amount of acetic acid in feces before ingestion of the *Salacia* extract powder is taken as 100.

TABLE 2

|  | Average pH of feces | Amount of acetic acid in feces |
|---|---|---|
| Before ingestion of *Salacia* extract powder | 7.6 | 100 |
| After ingestion of *Salacia* extract powder for 6 days | 8.0 | 150 |

As shown in Table 2, the average pH of feces did not decrease even after ingestion for 6 days as compared to before ingestion of the *Salacia* extract powder. In the case where the pH of feces is lower than pH 5.0, there is a concern that the activity of cellulose-degrading bacteria will be lowered, but ingestion of the *Salacia* extract powder does not have the above problem. In addition, by ingestion of the *Salacia* extract powder, the amount of acetic acid, a type of organic acid, in feces was increased. The acetic acid is known to promote intestinal peristaltic movement and to ameliorate the intestinal environment.

<Changes in the Number of Bacteria for Each Bacterium of the Genus *Lactobacillus*>

In addition, changes in the number of bacteria of the genus *Lactobacillus* were measured for each bacterial strain before ingestion of the *Salacia* extract powder and after ingestion of the *Salacia* extract powder for 6 days.

The changes in the number of bacteria were measured by the following method. The feces before and after the ingestion period were collected using a feces sampling kit (TechnoSuruga Laboratory Co., Ltd., Shizuoka, Japan). The collected feces were suspended in GTC (guanidine thiocyanate) Buffer (100 mmol/L Tris-HCl [pH 9.0], 40 mmol/L Tris-EDTA [pH 8.0], 4 mol/L Guanidine Thiocyanate). The feces added to the liquid were crushed with zirconia beads and DNA extraction was carried out from 100 µl of the suspension by using an automatic nucleic acid extractor (Precision System Science, Chiba, Japan). Using the obtained DNA, sample preparation for the sequencing library was carried out with a Nextera™ DNA sample preparation kit (Illumina Co., Ltd.). In addition, by adding an index sequence to each sample (according to the protocol of the kit), it was possible to discriminate the samples. Sequencing was carried out by the next generation sequencer (MiSeq; Illumina Co., Ltd.) using the prepared sequencer library. For the obtained data, quality check of the base sequence was carried out and filtering of low quality data was carried out. The data in which the quality check was cleared and the data with high similarity were divided into groups (Operation Taxonomic Unit (OTU)). For each OTU, a homology search was performed on the 16S rRNA gene database, and the lineage classification was estimated. The number of sequence data belonging to each classification group was tabulated and comparison of data before and after was performed. However, an abundance ratio differs greatly for each bacterium, and therefore an initial value was set to 1, and the number of bacteria after ingestion was taken as a relative value, and comparison of the number of bacteria before and after the ingestion was carried out. The results are shown in Table 3.

TABLE 3

|  | Lactobacillus equi | Lactobacillus hayakitensis | Lactobacillus equigenerosi | Lactobacillus delbrueckii | Lactobacillus ingluviei |
|---|---|---|---|---|---|
| Before ingestion of Salacia extract powder | 1 | 1 | 1 | 1 | 1 |
| After ingestion of Salacia extract powder for 6 days | 60 | 3 | 4 | 40 | 15 |

Based on the results shown in Table 3, it was proved that the Salacia extract powder has the effect of remarkably increasing the bacteria of the genus Lactobacillus originally contained in horses.

According to the present invention, the bacteria of the genus Lactobacillus, which are good bacteria, in the intestine of the domestic animal can be increased without externally administering bacteria, or preferably, harmful bacteria can be reduced. In addition, among bacteria called good bacteria, bacteria which lower an intestinal pH and impair the function of cellulose-degrading bacteria are also present, but in the present invention, preferably, it is possible to increase lactic acid bacteria which are good bacteria without lowering an intestinal pH.

According to the present invention, by administering at least one of the plant of the genus Salacia, the extract of the plant of the genus Salacia, or the ground product of the plant of the genus Salacia to the domestic animal, it is possible to stabilize the intestinal environment of the domestic animal, to prevent or treat digestive system diseases such as diarrhea and constipation, to relieve stress, to impart stress tolerance, to maintain health, to promote growth, to promote digestion and absorption, to improve feed efficiency, and/or to ameliorated a shape and odor of feces.

What is claimed is:

1. A method for promoting growth of a bacterium in the intestine of a horse in need thereof, comprising administering an effective amount of: a plant of the genus Salacia, an extract of the plant of the genus Salacia, or a ground product of the plant of the genus Salacia, and wherein the bacterium is the bacterium of the genus Lactobacillus and the bacterium is present in an intestine of the horse.

2. The method according to claim 1, wherein an average pH of feces after administration for 6 days is 6.0 to 8.2.

3. The method according to claim 1, wherein an amount of acetic acid in feces after administration for 6 days is increased by 1.1 times or more as compared to an amount of acetic acid in feces before administration.

4. The method according to claim 1, wherein the bacterium of the genus Lactobacillus is at least one selected from the group consisting of Lactobacillus equi, Lactobacillus hayakitensis, Lactobacillus equigenerosi, Lactobacillus delbrueckii, and Lactobacillus ingluviei.

5. The method according to claim 1, wherein administering to the horse as a horse feed.

6. The method according to claim 1, wherein administering to the horse as a horse supplement.

7. The method according to claim 1, wherein said effective amount is from 0.1 mg/kg/day to 2000 mg/kg/day.

8. The method according to claim 1, wherein intestinal bacterium of the genus Clostridium is lowered by 0.9 times or less, as compared to before said administration.

9. The method according to claim 1, wherein intestinal bacterium of the genus Clostridium is lowered by 0.6 times or less, as compared to before said administration.

* * * * *